(12) United States Patent
Sarwar et al.

(10) Patent No.: US 9,423,412 B2
(45) Date of Patent: Aug. 23, 2016

(54) AUTOMATIC ANALYZER

(75) Inventors: Sayaka Sarwar, Mito (JP); Shigeki Matsubara, Hitachinaka (JP); Kenji Teshigawara, Hitachinaka (JP); Emiko Suzuki, legal representative, Hitachinaka (JP); Osamu Matsumoto, Mito (JP); Sylvia Rosenblatt, Benediktbeuren (DE); Peter Wolf, Peissenberg (DE); Fridl Lang, Tutzing (DE); Roland Ihrig, Lampertheim (DE)

(73) Assignees: Hitachi High-Technologies Corporation, Tokyo (JP); Roche Diagnostics Operations Inc., Indianapolis, IN (US)

( * ) Notice: Subject to any disclaimer, the term of this patent is extended or adjusted under 35 U.S.C. 154(b) by 436 days.

(21) Appl. No.: 13/988,775

(22) PCT Filed: Nov. 28, 2011

(86) PCT No.: PCT/JP2011/077349
§ 371 (c)(1),
(2), (4) Date: Jul. 11, 2013

(87) PCT Pub. No.: WO2012/073877
PCT Pub. Date: Jun. 7, 2012

(65) Prior Publication Data
US 2013/0280130 A1    Oct. 24, 2013

(30) Foreign Application Priority Data
Nov. 29, 2010  (JP) ................................ 2010-265474

(51) Int. Cl.
*G01N 35/10*    (2006.01)
*G01N 35/00*    (2006.01)

(52) U.S. Cl.
CPC .... *G01N 35/1002* (2013.01); *G01N 35/00663* (2013.01); *G01N 2035/00673* (2013.01)

(58) Field of Classification Search
USPC .......................................................... 436/43
See application file for complete search history.

(56) References Cited

U.S. PATENT DOCUMENTS

| 7,749,441 | B2 | 7/2010 | Hanawa et al. |
| 2004/0253146 | A1* | 12/2004 | Shiba et al. .................... 422/64 |
| 2007/0255756 | A1 | 11/2007 | Satomura et al. |
| 2011/0090066 | A1* | 4/2011 | Yamaguchi et al. ....... 340/10.51 |

FOREIGN PATENT DOCUMENTS

| JP | 2000-310643 A | 11/2000 |
| JP | 2005-37171 A | 2/2005 |

(Continued)

OTHER PUBLICATIONS

International Preliminary Report on Patentability received in International Application No. PCT/JP2011/077349 dated Jun. 13, 2013.

*Primary Examiner* — Jill Warden
*Assistant Examiner* — Julie Tavares
(74) *Attorney, Agent, or Firm* — Mattingly & Malur, PC

(57) ABSTRACT

Unlike conventional reagent storing means of an analyzing unit having a cold-storage function, replacement reagent storing means having no cold-storage function requires reagent management of a higher order. An automatic analyzer is provided that manages the placing elapsed time for a reagent vessel in replacement reagent storing means 2, compares the placing elapsed time for the reagent with a permissible placing limit value stored as one of analysis parameters for each analysis item, and determines as to whether or not the placing elapsed time exceeds permissible limit value. In this way, the analyzer prevents the degradation of the reagent and automatically transfers the reagent to an analyzing section for performing measurement.

10 Claims, 2 Drawing Sheets

(56) References Cited

FOREIGN PATENT DOCUMENTS

| JP | 4033060 B2 | 11/2007 |
| JP | 2009-068992 A | 4/2009 |
| WO | 2006/009251 A1 | 1/2006 |
| WO | WO 2009142087 A1 * | 11/2009 |

* cited by examiner

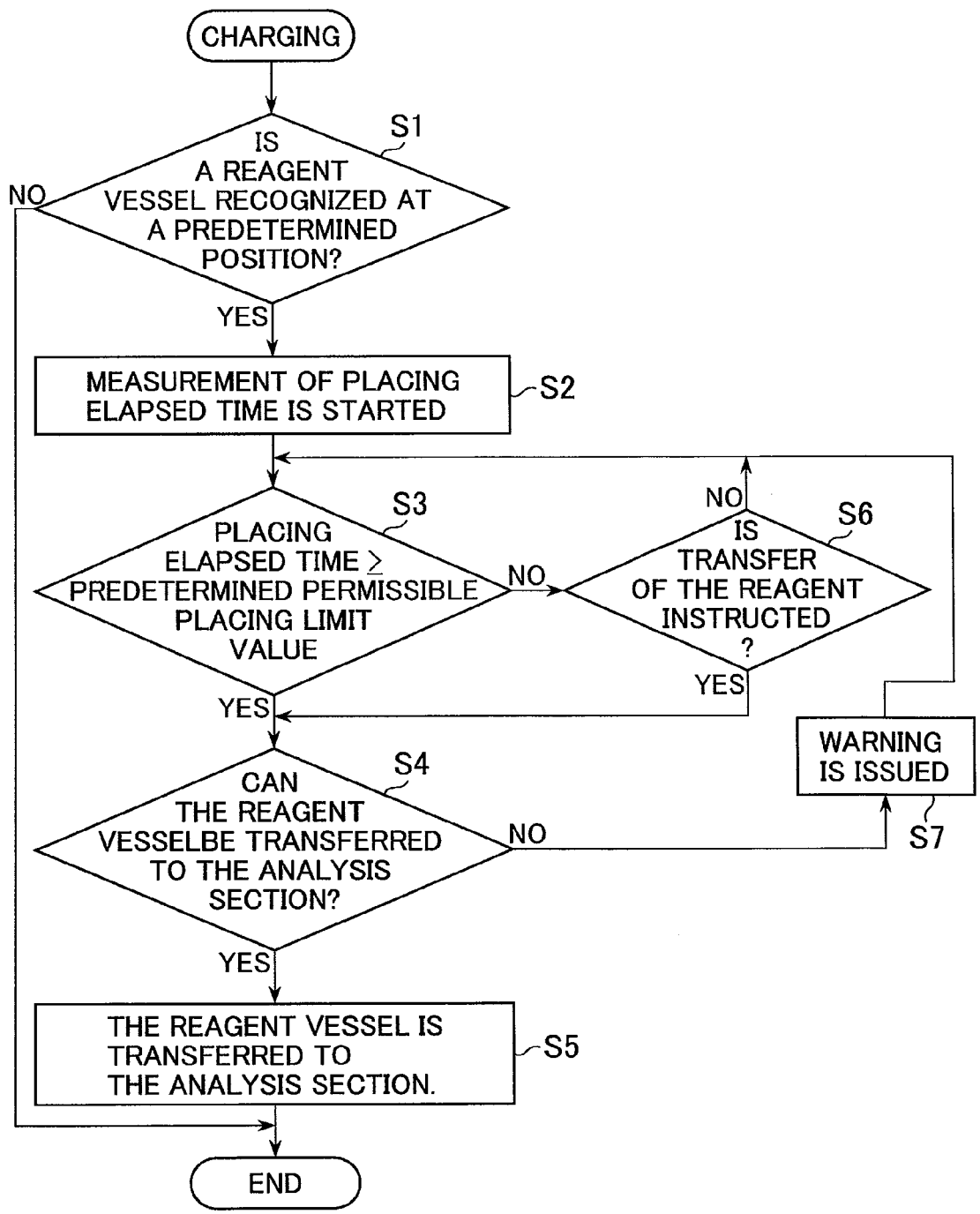

AUTOMATIC ANALYZER

TECHNICAL FIELD

The present invention relates to an automatic analyzer that analyzes a sample such as blood, urine or the like and in particular to an apparatus that replaces a reagent vessel.

BACKGROUND ART

Automatic analyzers which analyze samples such as blood, urine or the like are increased in the reagent consumption rate and in the frequency of replacing reagent vessels, along with the increased number of samples to be processed and increased measurement items. On the other hand, it is required to reduce operator's work as much as possible in order to reduce cost such as manpower expense. Thus, it is desired to simplify work for replacing a reagent vessel.

Also the sample processing speed by the automatic analyzer is largely increased, so that reagent exchanging work desires to minimize the interruption of analyzing operation without bringing the operation of the analyzer to a halt.

For example, in patent document 1, a replacement reagent storing means 2 is installed in addition to a reagent storing means 1 in an analyzing unit. Further, a reagent transfer means is installed between the replacement reagent storing means 2 and the reagent storing means 1 in the analyzing unit. In this way, it is intended to simplify reagent replacing work and to minimize the interruption of analyzing work.

PRIOR-ART DOCUMENT

Patent Document

Patent Document 1
 Japanese Patent No. 4033060

SUMMARY OF THE INVENTION

Problem to be Solved by the Invention

In patent document 1 mentioned above, if the replacement reagent storing means 2 does not have a cold storage function, there is concern that a reagent degrades as the elapsed time where the reagent vessel is placed in the replacement reagent storing means 2 is long. However, patent document 1 does not take into account elapsed time management after the reagent vessel has been set As regards the time management where the reagent is placed in the reagent storing means 1 having the cold storage function, management performed as described in e.g. JP-A-2000-310643 has been well-known. However, patent document 1 does not teach how to perform reagent management in the case where the reagent storing means 1 storing the reagent at cold temperatures and the storing means 2 storing the reagent at normal temperatures are mixed.

It is an object of the present invention to provide an automatic analyzer that prevents the degradation of a reagent and makes use of the reagent effectively in the case where a storing means 1 for storing a regent at cold temperatures and a storing means 2 for storing a reagent at normal temperature.

Means for Solving the Problem

Configurations of the present invention to achieve the above object are as below.

An automatic analyzer including: first reagent storing means for storing a plurality of reagent vessels; a reagent pipetting mechanism 37a -37d for pipetting a reagent from a reagent vessel stored in the first reagent storing means; and a measuring mechanism 39 for allowing the reagent and a sample to react with each other and measuring such a reacting liquid. The automatic analyzer is characterized by including: second reagent storing means for storing a plurality of reagent vessels; a reagent vessel transfer mechanism capable of transferring a reagent vessel selected from the reagent vessels stored in the second reagent storing means to the first reagent storing means; and a measuring means for measuring placing elapsed time of a reagent vessel in the second reagent storing means. The measuring means may be a computer for controlling the automatic analyzer.

The first reagent storing means may have a cold storage function and the second reagent storing means may have no cold storage function.

The second reagent storing means may be provided with means for reading 21 reagent information from a storage medium 35 attached to the reagent vessel. The placing elapsed time of the reagent vessel may be measured from a starting point, i.e., the time when the reagent information is read from the storage medium 35 attached to the reagent vessel loaded onto the second reagent storing means.

A permissible placing limit value for the reagent vessel in the second reagent storage means may be stored. Analysis parameters of a plurality of kinds of analysis items may be stored and the permissible placing limit value may be stored as one of the analysis parameters of the analysis items.

The permissible placing limit value may be read from a storage medium 35 of the reagent vessel. Alternatively, the automatic analyzer is connected to a remote computer 41 and the permissible placing limit value can be received from the remote computer 41. An information reading section 43 such as a disk drive which reads information from an external storage medium 42 such as CD or DVD may be provided and may read the permissible placing limit value from the external storage medium 42. Further, the permissible placing limit value is displayed on a screen 40 and can be edited on the screen 40.

Means is provided for detecting as to whether or not the placing elapsed time measured by the measuring means exceeds the permissible placing limit value. The means is a computer for controlling the automatic analyzer for example. Before the placing elapsed time for the reagent vessel will exceed the permissible placing limit value, reagent transfer means for transferring a reagent from the second reagent storing means to the first reagent storing means may transfer the reagent to the first reagent storing means.

In a case where the detecting means detect the fact that the placing elapsed time for the reagent vessel exceeds the permissible placing limit value, a warning may be issued and displayed on a screen 40. Further, when a reagent vessel in which the permissible placing limit value therefore is exceeded is used for analysis, a data alarm can be attached to an analysis result obtained by using the reagent vessel.

Reagent cap-opening means may be provided on at least one of the replacement second reagent storing means and the reagent transfer means. Means may be provided for opening the reagent vessel by use of the cap-opening means immediately before the reagent vessel is transferred by the reagent transfer means.

Instruction means may be provided for making an instruction to discharge the reagent vessel when the reagent vessel is not used for analysis in the case where the detecting means detects the fact that the placing permissible elapsed time exceeds the permissible limit value.

The placing elapsed time for the reagent vessel may be measured from a point of time when the reagent vessel is transferred into the second reagent means and may be stored.

The storage medium 35 may be any one of a bar code and RFID.

Effect of the Invention

The present invention can provide the automatic analyzer as below. Also in a case where the replacement reagent storing means 2 has no cold storage function, the placing elapsed time for the reagent vessel in the replacement reagent storing means 2 is managed. In addition to the expiration date for the reagent attached from the very beginning in the cold-storage environment, the permissible placing limit value in the not-cold-storage environment is stored as one of the analysis parameters. The placing elapsed time is compared with the permissible placing limit value. Thus, the reagent management of a higher order can be performed.

According to the present invention, the reagent management of a higher order is performed to achieve the saving of the reagent and sample and further to reduce the lowering of analysis accuracy due to abnormality.

The present invention can reduce operator's work burden such as re-measurement or the like due to the degradation of the reagent.

BRIEF DESCRIPTION OF THE DRAWINGS

FIG. 2 illustrates a flow of time management for reagent vessels in a replacement reagent storing means 2 by way of example.

MODE FOR CARRYING OUT THE INVENTION

Embodiments of the present invention will hereinafter be described with reference to the present invention.

Figure 1:
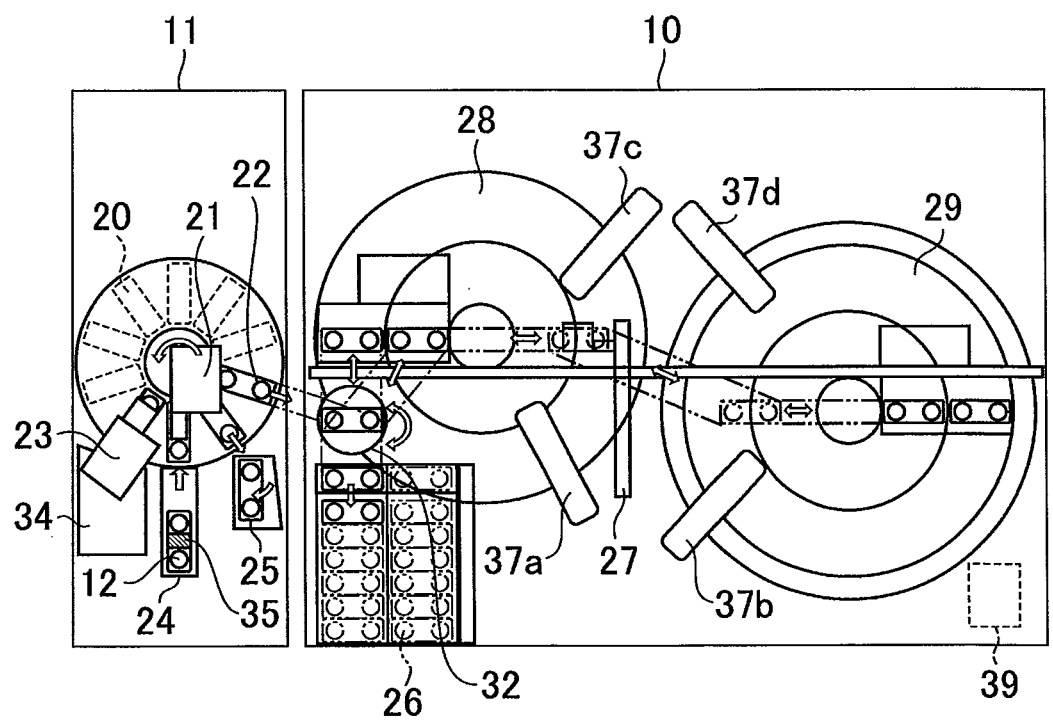
FIG. 1 is a plan view of an automatic analyzer according to the present invention.
Figure 1:
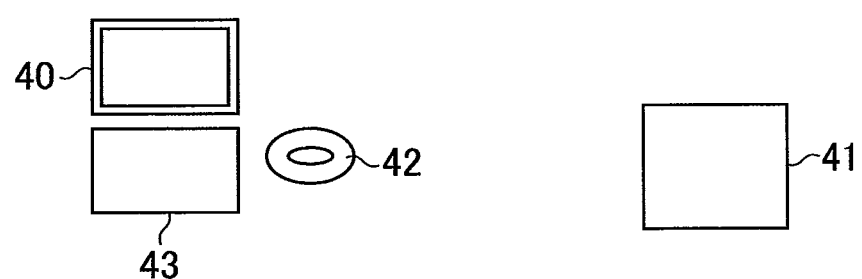

FIG. 1 is a plan view of an automatic analyzer.

The automatic analyzer is composed of an analyzing unit 10 and a buffer unit 11.

The analyzing unit 10 includes a reagent depository A28, a reagent depository B29, a reagent transfer mechanism 27 for transferring a reagent vessel 12 having been transferred from the buffer unit 11, to the reagent depository A28 or B29, and a reagent discharge-storage mechanism 26 for discharging a reagent vessel 12 on the analyzer unit 11 side. The buffer unit 11 includes a replenishment reagent depository 20 which temporarily holds a replenishment reagent and a reagent discharge mechanism 25 which discharges reagent vessels.

A description is given of a procedure for transferring reagent vessels 12 by use of this apparatus.

An operator first puts a reagent vessel 12 at a reagent charging port not illustrated in the figure. The reagent vessel 12 is then transferred to the replenishment reagent depository 20 by a reagent replenishing mechanism 24.

A RFID tag in which information such as a reagent residual quantity, a lot, an expiration date, etc. are recorded is attached to the reagent vessel 12 having been transferred to the replenishment reagent depository 20. Such information is read by a reagent information read/write mechanism 21 installed on the upper side of the replenishment reagent depository 20 and is stored in a control computer not illustrated in the figure. In this case, when the control computer determines that a certain reagent vessel 12 is unusable for analysis because of expiration, reagent residual shortage, etc., such a reagent vessel 12 is discharged by the reagent discharge mechanism 25 provided in the buffer unit 11.

The reagent requested for replenishment is transferred to a cap opening position of a reagent cap opening mechanism 23 within the replenishment reagent depository 20 on which reagents have previously been mounted. A reagent cap of the reagent vessel 12 is then opened at the cap opening position and is discarded into a reagent cap discard box 34.

The reagent vessel 12 (hereinafter, also referred to as the reagent cassette or reagent bottle) whose reagent cap has been opened is transferred to a reagent vessel delivery position in the replenishment reagent depository 20. Such a reagent vessel is transferred from the buffer unit 11 to the analyzing unit 10 by the reagent vessel transfer mechanism 22. Incidentally, if the timing of reagent replacement is within a range where reagent shortage does not occur, the reagent replacement is performed using a vacant cycle between sample transfers or time between first regent dispensing and second reagent dispensing. If the reagent replacement is not made in time by any means, specimen sampling is interrupted and a reagent vessel is placed after the reagent is dispensed into the specimen prior to the interruption. In any of these cases, the state of the analyzer is under analysis. In other words, the analyzer is not temporarily stopped to replenish the reagent. Therefore, the time of the analysis interruption can be shortened.

The reagent cassette 12 having been transferred to the analyzing unit 10 is set in a reagent turning mechanism 32 installed in the analyzing unit 10. The reagent turning mechanism 32 changes the direction of the reagent bottle 12 in a direction necessary to mount the reagent cassette 12 in the reagent depository A28 or B29.

The reagent bottle 12 whose direction has been changed is transferred by the reagent transfer mechanism 27 to one of the reagent depositories A28 and B29 that has been requested to replace the reagent. After having been transferred the reagent bottle 12 to the reagent depository A28 or B29, the reagent transfer mechanism 27 transfers a reagent vessel 12 to be replaced because of a small residual amount of reagent, from the reagent depository A28 or B29 to the reagent discharge-storage mechanism 26, i.e., in an opposite manner. The reagent discharge-storage mechanism 26 transfers the reagent vessel 12 to a reagent storing portion in the reagent discharge-storage mechanism 26. In addition, the reagent vessel 12 is stored thereat until it will be picked out by an operator.

A detailed description is hereinafter given of reagent management in the replenishment reagent depository 20 by use of this apparatus.

As described above, a plurality of kinds of analysis items have reagent information for each of the analysis items. The analysis information includes the conventional reagent information such as reagent ID, lot information, a pipetting amount of reagent pipetted during measurement and the like. In addition to the above-mentioned reagent information, the analysis information includes information about a permissible placing limit value for the replenishment reagent depository 20 which does not correspond to a cold storage environment. This permissible placing limit value is set as an initial value for each analysis item similarly to an expiration date in the normal cold storage environment.

Although depending on an analysis item, the analysis item may be set by the hour at a numerical value from 0 to 24 or by the minute at a numerical value from 0 to 1440. In this case, the measurement of the placing elapsed time for the reagent vessel in the replenishment reagent depository 20 is started from the point of time when the reagent information is read by the reagent information reader mechanism 21. Incidentally, it is preferred that the timing of the measurement-start be the point of time when the reagent vessel 12 is set at the reagent charging port of the reagent transfer mechanism 24.

The permissible placing limit value included in the reagent information is set as an initial value. However, in view of environmental conditions, seasonal conditions and other conditions in each of facilities, the permissible placing limit value in the reagent information may be made editable on a display screen 40 or the like by an operator for the purpose of reagent management of a higher order on the basis of the respective environmental conditions or of operator's reagent management consciousness.

A control computer not illustrated uses the permissible placing limit value included in reagent information and the measured placing elapsed time in the replenishment reagent depository 20 to determine whether or not the placing elapsed time exceeds the permissible placing limit value. Before the placing elapsed time exceeds the permissible placing limit value, the reagent vessel 12 is transferred by the reagent transfer mechanism 27 from the replenishment reagent depository 20 to the reagent depository A28 or B29 in the analyzing unit 10. For example, if the placing elapsed time approaches the permissible placing limit value within one hour, then the reagent vessel 12 becomes a candidate to be transferred from the replenishment reagent depository 20 to the reagent depository A29 or B29 in the analyzing unit 10. In order to transfer the reagent vessel from the replenishment reagent depository 20 to the reagent depository A28 or B29 in the analyzing unit 10, it is supposed that the reagent vessel is not allowed to interfere with a mechanism such as a reagent prove or the like in the analyzing unit 10. Therefore, the interruption of analysis due to replacement will lower the processing capacity of the analyzer. If the reagent vessel becomes the transfer candidate, it can be transferred using the opportunity of the transfer of the reagent vessel on the basis of timing of the transfer with the analyzing unit stopped because of another factor with an increased urgent necessity in which the residual amount of the reagent vessel in the reagent depository in the analyzing unit 10 becomes small. Therefore, the analysis interruption due to replacement can be minimized to maintain the processing capacity.

Further, for example, the permissible placing limit value of the reagent vessel 12 may previously be equal to 0, i.e., the permissible placing limit value in the replenishment reagent depository 20 may be 0 hour or 0 minute. In such a case, it is determined whether or not the reagent vessel 12 can be transferred to the reagent depository A28 or B29 in the analyzing unit 10 by the reagent transfer mechanism 27 as early as possible. The placing permissible residual time may be equal to 0 hour/minute or below. In such a case, to make it possible to transfer the reagent vessel to the analyzing unit, the reagent management enters a sampling stop mode. (If a rack on a transfer line in an analyzing section finishes dispensing of a sample and then dispensing of a R2/R3 reagent probe,) the reagent vessel is transferred to the reagent depository A28 or B29 in the analyzing unit. In this case, the reagent vessels can be transferred in order of priority based on the setting values. When the reagent vessel is placed in the replenishment reagent depository 20, it is desired that the reagent vessel be stored with its cap closed in order to prevent degradation of the reagent. Therefore, it is desired that the reagent cap be opened just prior to the transfer.

If the measured placing elapsed time of the reagent vessel 12 exceeds the permissible placing limit value by any means, a warning is displayed on the display screen 40 to inform an operator about it. In this case, when the reagent vessel 12 is not used for analysis, the operator can allow the display screen 40 to instruct the reagent discharge mechanism 25 to transfer the reagent vessel 12 for discharge. When the operator instructs that the reagent is used for analysis, the reagent cap of the reagent vessel 12 can be opened at the cap opening position and the reagent vessel 12 is transferred to the analyzing unit 10. Incidentally, the reagent that has exceeded the permissible placing limit value and has been used for measurement is allowed to have a measurement result attached with a date alarm. Incidentally, the placing elapsed time to which a data alarm is to be attached may be able to be set on the screen 40. In a case where the reagent vessel is transferred toward the analyzing unit 10 after the sampling stop has been performed, a time taken until the completion of dispensing operation is estimated at about 30 minutes. For example, it is desirable that an operator be able to set from the screen 40 the fact that a data alarm is not attached to the measurement result obtained using the reagent whose placing elapsed time has exceeded the permissible placing limit value by 0 to 0.5 hour.

The relationship between the measurement result of a sample and a state of the reagent can be also grasped by writing the recorded result of the measured housing elapsed time for the reagent vessel 12 into a storage medium such as a RFID attached to the reagent vessel 12. Further, it is conceivable that the reagent vessel that has been once placed in the replenishment reagent depository 20 for a certain period of time by the instruction of the operator may be discharged without being transferred toward the analyzing unit 10. In such a case, the recorded result of the placing elapsed time in the replenishment reagent depository 20 is stored in the RFID attached to the reagent vessel. If the reagent vessel is again loaded onto the replenishment reagent depository 20, the placing elapsed time is continuously measured as an accumulated time added with the placing elapsed time previously stored in the RFID. Therefore, the reagent vessel can be transferred to the analyzing unit side reagent depository as early as possible even if the placing elapsed time of the reagent vessel approaches the permissible placing limit value within 0 or 0.5 hour at the point of time when the reagent vessel is transferred into the replenishment reagent depository 20.

FIG. 2 is a flow chart illustrating the details of the reagent management after a reagent vessel is loaded onto replacement reagent storage means 2 according to the present invention.

It is first recognized that the reagent vessel has been loaded onto the replacement reagent storage means 2 (step S1).

The measurement of the placing elapsed time in a second reagent storing means is started from a starting point, i.e., the time when the reagent vessel is recognized (step S2).

The placing elapsed time is added as a variable by the minute or by the time.

Next, a determination as to whether or not the placing elapsed time of the reagent vessel exceeds a predetermined permissible placing limit value is made by comparing the placing elapsed time of the reagent vessel with the predetermined permissible placing limit value (step S3).

When the placing elapsed time of the reagent vessel exceeds the predetermined permissible placing limit value, a determination as to whether or not the reagent vessel can be transferred to the analyzing section is made at step S4. When possible, the reagent vessel is transferred to the analyzing section (step S5).

When impossible, a warning is issued at step S7. Then, a comparison between the placing elapsed time and the predetermined permissible placing limit value is further continued (step S3).

At step S3, when the placing elapsed time of the reagent does not exceeds the predetermined permissible placing limit value, the presence or absence of instruction to transfer the reagent is checked with the control computer not illustrated (step S6).

When there is no instruction to transfer the reagent, the measurement of the placing elapsed time is continued and the comparison between the placing elapsed time and the predetermined placing permissible value is continued (step S3).

At step 6, when there is an instruction to transfer the reagent, a determination is made as to whether or not the reagent can be transferred to the analyzing section at the subsequent step, i.e., at step S4. When possible, the reagent is transferred to the analyzing section at step S5. When impossible, the comparison between the placing elapsed time and the predetermined placing limit value is further continued (step S3).

EXPLANATION OF REFERENCE NUMERALS

10 Analyzing unit
11 Buffer unit
12 Reagent vessel
20 Replenishment reagent depository
21 Reagent information reader mechanism
22 Reagent transfer mechanism
23 Reagent cap opening mechanism
24 Reagent replenishment mechanism
25 Reagent discharge mechanism
26 Reagent discharge-storage mechanism
27 Reagent transfer mechanism
28 Reagent depository A
29 Reagent depository B
32 Reagent turning mechanism
34 Reagent cap discard box
35 Storage medium
37 Reagent pipetting mechanism
39 Measuring mechanism
40 Screen
41 Remote computer
42 External storage medium
43 Information reading section

The invention claimed is:

1. An automatic analyzer comprising:
an analyzing unit, comprising:
  a first reagent depository configured to store a plurality of reagent vessels;
  a reagent pipetting mechanism configured to pipette a reagent from a reagent vessel stored in the first reagent depository; and
  a measuring mechanism configured to measure a reaction of a reagent and a sample;
a buffer unit, comprising:
  a second reagent depository configured to store a plurality of reagent vessels;
  a reagent discharge mechanism configured to discharge a reagent vessel stored in the second reagent depository; and
  one of a radio-frequency identification (RFID)reading device and a barcode reading device configured to read a storage medium attached to each of the reagent vessels at the second reagent depository,
a reagent vessel transfer mechanism configured to transfer a reaction vessel from the second depository to the first reagent depository and the reagent discharge mechanism; and
a control computer, having a memory coupled to a processor, connected to each of the reagent pipetting mechanism, the measuring mechanism, the reagent vessel transfer mechanism, and the one of the radio-frequency identification (RFID) reading device and the barcode reading device,
wherein the memory stores a storage time limit value corresponding to a reagent held in a reagent vessel,
wherein the processor is configured to execute instructions stored in the memory such that the processor is configured to:
acquire a storage time limit value corresponding to a reagent held in a reagent vessel in the second reagent depository from the memory,
control the one of the radio-frequency identification (RFID) reading device and the barcode reading device to read the reagent information from the storage medium on a reagent vessel and store a first time into memory when the reagent information is read,
calculate an elapsed time that has elapsed from the first time and store it as an elapsed time in the memory,
determine whether the elapsed time is greater than or equal to the storage time limit value,
determine if the elapsed time is within a predetermined amount of time of the storage time limit value for a reagent held by a reagent vessel,
if the elapsed time is within the predetermined amount of time of the storage time limit value for a reagent held by the reagent vessel, control the reagent vessel transfer mechanism to transfer the reagent vessel to the first reagent depository,
if the elapsed time is greater than or equal to the storage time limit value, control the reagent vessel transfer mechanism to transfer the reagent vessel to the discharge mechanism, and
control the measuring mechanism to measure a reaction of a sample and a reagent of the reagent vessel transferred to the first reagent depository.

2. The automatic analyzer according to claim 1, wherein the first reagent depository is configured to cool the reagents held by the plurality of reaction vessels stored in the first reagent depository.

3. The automatic analyzer according to claim 1, wherein the reagent information read from the storage medium attached to each of the plurality of reagent vessels includes the storage time limit value.

4. The automatic analyzer according to claim 1, wherein the automatic analyzer is connected to a remote computer from which the storage time limit value is acquired.

5. The automatic analyzer according to claim 1, further comprising a display, which is interfaced with the control computer,
wherein the control computer is further programmed to display the storage time limit value on the display.

6. The automatic analyzer according to claim 5,
wherein the control computer is further programmed to accept an input to edit the storage time limit value stored in the control computer.

7. The automatic analyzer according to claim 5,
wherein the control computer is further programmed to, if the elapsed time is greater than or equal to the storage time limit value, display a warning on the display.

8. The automatic analyzer according to claim 5,
the control computer is further programmed to, if the elapsed time is greater than or equal to the storage time limit value, associate a measurement result obtained by the measuring mechanism with an alarm.

9. The automatic analyzer according to claim 1, further comprising:
a reagent cap-opening mechanism disposed on at least one of the second reagent depository and the reagent transfer mechanism,
wherein the control computer is further programmed to control the reagent cap-opening mechanism to open a cap of a reagent vessel before the reagent vessel is transferred by the reagent transfer mechanism.

10. The automatic analyzer according to claim 1, wherein the storage medium is one of a bar code and an RFID medium.

* * * * *